United States Patent [19]

Angelini et al.

[11] Patent Number: 5,236,448
[45] Date of Patent: Aug. 17, 1993

[54] HEART VALVE PROSTHESIS

[75] Inventors: Gianni Angelini, St. Fagans, United Kingdom; Claudio Pistolesi, Siena, Italy

[73] Assignee: Cardio Carbon Company Ltd., Swansea, United Kingdom

[21] Appl. No.: 690,936
[22] PCT Filed: Jan. 26, 1990
[86] PCT No.: PCT/GB90/00121
§ 371 Date: Jul. 10, 1991
§ 102(e) Date: Jul. 10, 1991
[87] PCT Pub. No.: WO90/08518
PCT Pub. Date: Aug. 9, 1990

[30] Foreign Application Priority Data

Jan. 26, 1989 [GB] United Kingdom ................. 8901733

[51] Int. Cl.$^5$ ................................................ A61F 2/24
[52] U.S. Cl. .................................................... 623/2
[58] Field of Search ........................................ 623/2

[56] References Cited

U.S. PATENT DOCUMENTS

| | | |
|---|---|---|
| 3,926,215 | 12/1975 | Macleod ........................ 623/2 X |
| 4,178,638 | 12/1979 | Meyer ............................ 623/2 |
| 4,349,498 | 9/1982 | Ellis et al. . |
| 4,352,211 | 10/1982 | Parravicini . |
| 4,377,010 | 3/1983 | Fydelor et al. ................. 623/2 X |
| 4,597,767 | 7/1986 | Lenkei ............................ 623/2 |
| 4,820,299 | 4/1989 | Philippe et al. ................ 623/2 |
| 4,822,353 | 4/1989 | Bokros ............................ 623/2 |
| 4,863,458 | 9/1989 | Bokros ............................ 623/2 |

FOREIGN PATENT DOCUMENTS

| | | |
|---|---|---|
| 0055406 | 7/1982 | European Pat. Off. . |
| 1167329 | 10/1969 | United Kingdom . |
| 8802247 | 4/1988 | World Int. Prop. O. ........... 623/2 |

OTHER PUBLICATIONS

J. C. Bokros, "Carbon Biomedical Devices", 1977, *Carbon*, vol. 15, pp. 355-371.

*Primary Examiner*—Randall L. Green
*Assistant Examiner*—D. Willse
*Attorney, Agent, or Firm*—Merchant, Gould, Smith, Edell, Welter & Schmidt

[57] ABSTRACT

The prosthesis comprises a unitary annular valve body having a pair of leaflets (2, 3) mounted on pivot posts adjacent their outer edges, so as to pivot between a closed position (in which the free edges of the leaflets (2, 3) are contiguous so as to inhibit flow of blood through the valve body) and a fully open position (in which the free edges are parallel to one another so as to permit flow of blood through the valve body). The valve body and the leaflets (2, 3) are each precision moulded, homogenous monolithic vitreous carbon artifacts having an as moulded surface of optical quality.

10 Claims, 2 Drawing Sheets

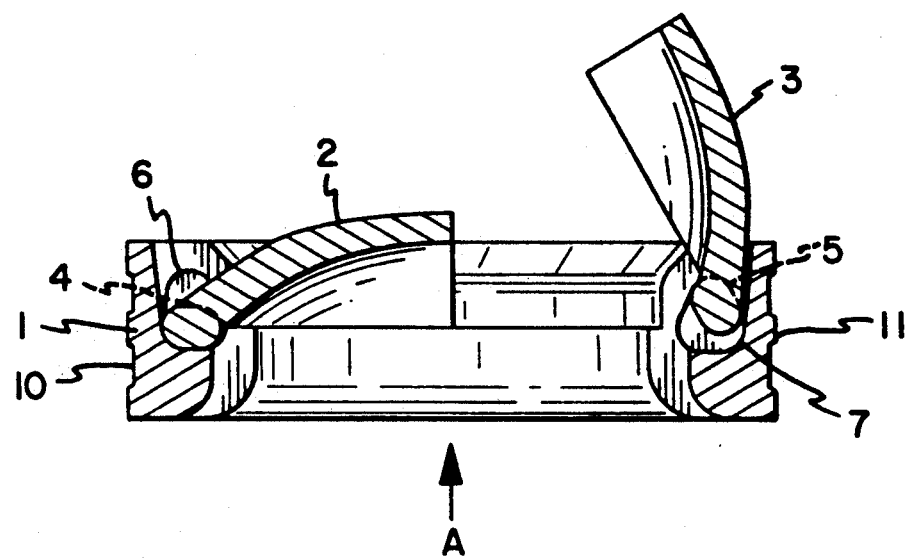
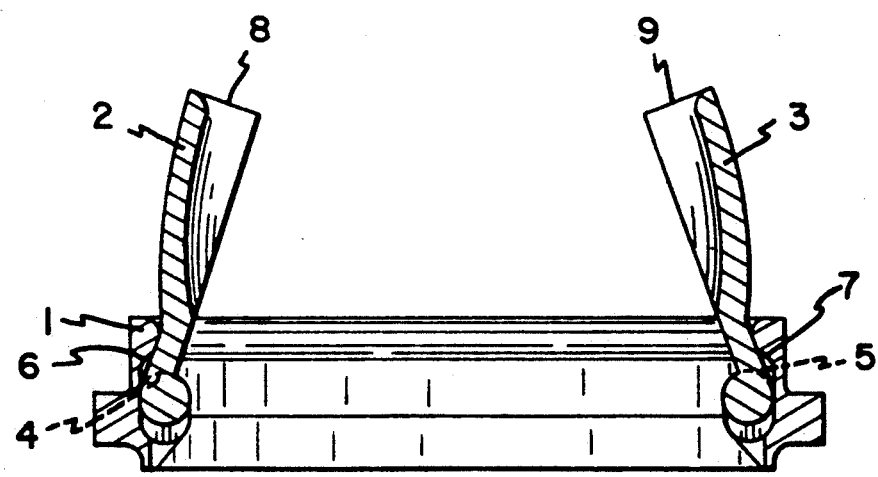

HEART VALVE PROSTHESIS

The present invention is concerned with heart valve prostheses.

Various types of synthetic heart prosthesis are known which operate haemodynamically when used in the surgical replacement of a heart valve, such as the mitral or aortic valve.

One known type of heart valve prosthesis is the St. Jude valve, which comprises a valve body having a passageway for the flow of blood therethrough from upstream to downstream, and a pair of flat leaflets which are pivotally supported in the passageway and movable between a closed position inhibiting blood flow and an open position permitting blood flow therethrough.

Another known type of heart valve prosthesis is the Duramedics valve which is a bileaflet valve in which the leaflets are curved in a plane parallel to the pivot axis of the leaflets.

Such heart valve prostheses have peripheral pivot points, the pivot axes being substantially parallel to the junction between the two leaflets, and each axis defining a chord on the respective leaflet. Such heart valve prostheses all have points of weakness at the pivot points, which can cause catastrophic failure and/or promote blood coagulation. Moreover, the leaflets provide obstructions to the flow of blood through the valve and substantially disturb the laminarity of such blood flow.

It has been previously proposed, in broad terms, that vitreous carbon would be a suitable material for the production of heart valve prosthesis. Vitreous carbon artefacts are produced by careful, controlled pyrolysis of resin mouldings is described in "Polymeric Carbons, Carbon Fibre, Glass and Char" by G. Jenkins and K. Kawamura, Cambridge University Press, 1976. In this method, the resin material (such as a phenolic resin or furan resin) is cast and cured as a block, machined to the form of the final artefact, and then slowly pyrolysed over a prolonged period.

We have now devised an improved bileaflet heart valve prostheses, which enables the properties of vitreous carbon, both during the pyrolysis process, and in the resulting artefact, to be optimised.

According to the present invention, therefore, there is provided a heart valve prosthesis comprising a unitary annular valve body having a passageway for the flow of blood therethrough from upstream to downstream, and a pair of leaflets pivotally mounted in said valve body for pivotal movement between a closed position, in which closed position said leaflets lie contiguous with one another so as to obturate said passageway to the flow of blood therethrough, and a fully open position, in which the inner edges of said leaflets are substantially parallel to one another in a downstream position, so as to permit blood flow through said passageway, each of said leaflets being pivotally mounted adjacent the outer edge thereof about a pivot axis which is substantially parallel to said inner edges and which does not intersect the respective leaflet, in which each of said leaflets and said valve body is a precision moulded, homogeneous monolithic vitreous carbon artefact having an as-moulded surface of optical quality.

The valve body and the leaflets have, in the as-moulded state, all the surface characteristics of the mould surfaces; further machining or polishing is generally unnecessary and, indeed, undesirable. The mould surfaces employed to produce the vitreous carbon artefacts are therefore of optical quality. By optical quality, we mean herein a surface finish with a centre-line average (Ra) of less than 0.05 micrometers.

The annular valve body and the leaflets are all homogeneous (that is, they are essentially free of granular or powdered filler, fibrous reinforcement, or other inclusions). They are further monolithic, being devoid of any coating, and have a purity of substantially 100% (that is, less than about 50 ppm of impurities). The valve body and the leaflets are generally impermeable to helium and heavier gases.

The bileaflet heart valve prosthesis according to the invention is generally such that the passageway formed when the leaflets are in the fully open position is substantially free of any transverse obstruction to the blood flow; it is particularly preferred that the spacing between the inner edges of the leaflets is at least as great as the spacing between the axes about which the leaflets pivot.

The leaflets are preferably symmetrical and generally semi-circular or semi-elliptical when viewed in plan; it is particularly preferred that each of the leaflets is shaped for substantially non-turbulent passage of blood along both faces thereof when the leaflets are in the fully open position. It is preferred that both faces of the leaflets should be in the form of continuous smooth curves; it is further preferred that in the closed position the leaflets should present a generally concave surface when viewed from upstream.

In the latter closed position, the leaflets are preferably wholly contained within the upstream and downstream limits of the valve body, as are the relevant pivot structures. The latter are preferably upstream of the median plane of the valve body, whereby the protrusion of the leaflets from the valve body in the fully open position can be minimised, with consequent minimisation of impongement of the leaflets with muscle and other tissue.

The valve body will generally be held in place by means of a peripheral sewing ring; the latter is preferably retained on the valve body with the aid of a plurality of spaced grooves provided around the circumferential periphery of the valve body.

In one preferred embodiment of the invention, the pivot axes of the respective leaflets are substantially parallel to opposed external faces of the valve body. It is further particularly preferred that the pivot axes should be substantially perpendicular to opposed transverse external faces of the valve body (that is, there are preferably two pairs of generally parallel external faces for the valve body); adjacent ones of the external faces are generally connected by smoothly curved portions, such that the whole external shape is generally rectangular with curved corners. It is a feature of the present invention that the external faces of the valve body which are parallel to the pivot axes of the leaflets may be longer than the external faces perpendicular thereto; that is, unlike the conventional circular valve body, the valve body employed in the valve according to the invention need not be axially symmetrical.

Such a geometry enables the "effective orifice area" (that is, the ratio of the internal diameter to the external diameter) to be increased relative to a conventional circular occluder ring. This enables the size of valve which can be implanted in a patient to be maximised, thereby optimising the volume of blood flowing through the valve during use.

The vitreous carbon artefacts (that is, the valve body and the pair of leaflets) are generally produced by a process comprising partially curing a substantially water-free phenolic resin in ambient atmosphere; precision moulding the partially cured phenolic resin in an enclosed mould having moulding surfaces of optical quality (as defined above), which are preferably such that the resulting moulding has a maximum thickness not exceeding 6 millimeters, under such conditions that the resulting moulding is substantially fully cured, substantially pore-free, and transparent; gradually heating the resulting moulding in a non-oxidising atmosphere over a period of at least twenty hours to final temperature of at least 1000° C.; and maintaining the final temperature until the moulding is substantially fully carbonized to vitreous carbon.

In the phenolic resin used in the method just described, the phenol/aldehyde ratio is generally slightly greater than 1:1 (such as 1.1 to 1.8:1), that is, a resol. An inappropriate phenol:aldehyde ratio may cause cracking of the final artefact. The phenol may be phenol itself, a cresol, xylenol or the like. The aldehyde is typically formaldehyde. Before the step of partial curing in ambient atmosphere, the resin should be rendered as free of water as possible so as to minimise porosity in the resulting artefact (if water is not eliminated, the resulting artefact could contain pores typically of size around 50 microns).

The water may be removed by any suitable method, preferably by the combined action of heat and reduced pressure (for example, in a rotary evaporator) whereby the water will be boiled off; alternatively, an azeotropic mixture can be formed which may allow the water to be removed at a lower temperature.

The moulding stage (typically compression or transfer moulding) may employ moulds with glass, polished metal, or other suitable optical quality surfaces. Metal surfaces, such as surfaces of high quality steel, are preferred.

Transfer moulding is preferred, and is preferably carried out so that the resin is raised to a temperature of greater than 100° C., for example, about 160° C., such that substantially complete cure can take place within the mould. Shortly after removal from the mould, the moulding may, if desired, be given a permanent deformation.

The carbonisation of the moulding can be considered as three successive stages. At lower temperatures (such as 300° C. to 500° C.), there is considerable gas evolution, and consequent weight loss; at higher temperatures (such as from 450° to 600° C.), there is rearrangement of the molecular structure and consequent shrinkage; while at even higher temperatures residual hydrogen is driven off.

The rate of temperature rise during carbonisation should be closely controlled, the optimum rate depending on the thickness and other dimensions of the artefact, and the temperature. Artefacts with a thickness greater than 6 millimeters cannot be satisfactorily carbonised, whereas for artefacts with a thickness of about 4 millimeters, the temperature rise at lower temperatures (such as up to 650° C.) is typically of the order of a few degrees Celsius (such as 5°-20° C.) per hour. The rate of temperature increase at higher temperatures is less critical, and at such higher temperatures the rate of increase may be of the order of a hundred degrees Celsius per hour.

The non-oxidising atmosphere may be an inert gas such as argon, helium or nitrogen, optionally in admixture with a minor amount of hydrogen.

The fact that the method described above involves substantial shrinkage during carbonisation is advantageous, as will now be described. Specifically, the pair of leaflets are initially formed with integral trunnion structures adjacent an edge of each leaflet permitting pivotting of the leaflets in an appropriately shaped annular valve body; the valve body is then formed and shrunk around the leaflets such that complementary formations in the occluder ring seat the trunnion structures provided on the leaflets to permit pivotting of the leaflets. The pivot axis about which a respective trunnion structure is pivotal is substantially parallel to the inner edge of the leaflet and does not intersect the respective leaflet. That is, each pivot axis is either tangential to, or outside the periphery of, the respective leaflet.

This method of production involving controlled shrinkage offers a high degree of structural integrity for the resulting valve structure, and minimises the possibility of inadvertent separation of a leaflet from the valve body; no further securing of the valve leaflets is therefore required.

Preferred embodiments of the present invention will now be described with reference to the accompanying drawings, in which:

FIG. 2 is a sectional view through the valve of FIG. 2; and

FIG. 3 is a sectional view through an alternative valve in which the leaflets are in the fully open position.

Figure 1:
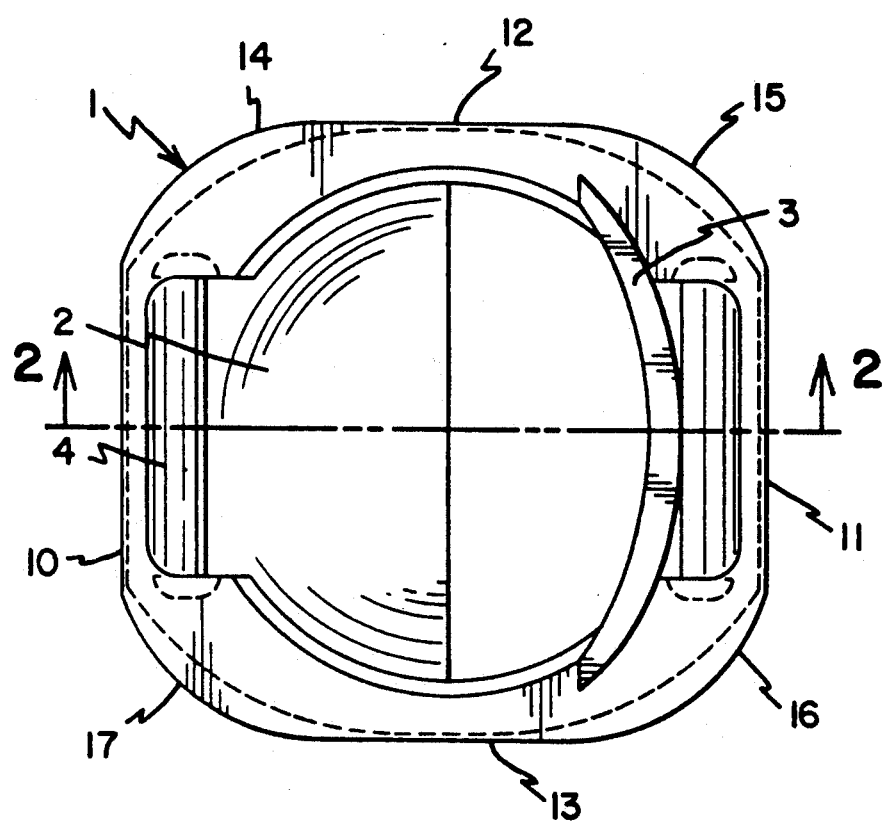
FIG. 1 is a plan view of an exemplary heart valve according to the invention with (for illustration purposes only) one leaflet in the open position and the other in the closed position.

Referring to FIGS. 1 and 2, the illustrated valve comprises a valve annulus 1 (also known as an occluder ring) having a pair of generally semi-circular (when viewed in plan) leaflets 2,3 each having a peripheral extension 4,5 at the edge thereof. The peripheral extensions serve as pivot posts or trunnions, and are seated in respective seating structures 6,7 provided in valve annulus 1.

Leaflets 2,3 are concave when viewed in the direction of arrow A (from the upstream direction when in their closed position) and convex when viewed from downstream. Each face is in the form of a smooth continuous curve, such that blood can flow in a non-turbulent manner over both faces when the leaflets are in their open positio.

In the embodiment of FIGS. 1 and 2, the valve annulus 1 is generally rectangular in plan view, having a first pair of parallel external faces 10,11 which are parallel to the axes of extensions 4,5 and a second pair of external faces 12,13 perpendicular thereto. The corners 14,15,16,17 are smoothly rounded off.

Referring to FIG. 3, the alternative heart valve illustrated has different seating structures 6,7 to those of FIGS. 1 and 2. The valve is shown with both leaflets 2,3 in the full open position. In this position it will be noted that the free edges 8,9 are separated by an amount equal to the spacing between the pivot posts or trunnions. In this position, the passageway through the valve is, as shown, free of any transverse obstruction to the flow of blood therethrough.

We claim:

1. A heart valve prosthesis comprising a unitary annular valve body having a passageway for the flow of blood therethrough from upstream to downstream, and a pair of leaflets pivotally mounted in said valve body for pivotal movement between a closed position, in which closed position said leaflets lie contiguous with one another so as to obturate said passageway to the flow of blood therethrough, and a fully open position, in which inner edges of said leaflets are substantially parallel to one another in a downstream position, so as to permit blood flow through said passageway, each of said leaflets being pivotally mounted adjacent an outer edge thereof about a pivot axis which is substantially parallel to said inner edges and which does not intersect the respective leaflet, in which said leaflets and said valve body are precision moulded, homogeneous monolithic vitreous carbon artifacts having an as-moulded surface of optical quality.

2. A heart valve prosthesis according to claim 1, wherein the passageway formed when the leaflets are in the fully open position is substantially free of any transverse obstruction to the blood flow.

3. A heart valve prosthesis according to claim 1, wherein the spacing between said inner edges when said leaflets are in said fully open position is not substantially less than the spacing between the axes about which the leaflets pivot.

4. A heart valve prosthesis according to claim 1 wherein said leaflets are symmetrical and generally semi-circular or semi-elliptical when viewed in plan.

5. A heart valve prosthesis according to claim 1, wherein faces of each leaflet are in the form of respective continuous curves.

6. A heart valve prosthesis according to claim 1, wherein said leaflets present a generally concave surface in the closed position when viewed from upstream.

7. A heart valve prosthesis according to claim 6, wherein leaflets are wholly contained within upstream and downstream limits of the valve body when in the closed position.

8. A heart valve prosthesis according to claim 1, in which said pivot axes are substantially parallel to opposed external faces of said valve body.

9. A heart valve prosthesis according to claim 1, in which said pivot axes are substantially perpendicular to opposed transverse external faces of said valve body.

10. A heart valve prosthesis according to claim 1, in which a plurality of spaced grooves are provided around the circumferential periphery of the valve body.

* * * * *